United States Patent [19]
Gullberg et al.

[11] Patent Number: 5,338,936
[45] Date of Patent: Aug. 16, 1994

[54] SIMULTANEOUS TRANSMISSION AND EMISSION CONVERGING TOMOGRAPHY

[75] Inventors: Grant T. Gullberg, Salt Lake City, Utah; Hugh T. Morgan, Highland Heights, Ohio; Chi-Hua Tung, Salt Lake City, Utah; Gengsheng L. Zeng, Salt Lake City, Utah; Paul E. Christian, Salt Lake City, Utah

[73] Assignee: Thomas E. Kocovsky, Jr., Cleveland, Ohio

[21] Appl. No.: 27,882

[22] Filed: Mar. 8, 1993

Related U.S. Application Data

[63] Continuation-in-part of Ser. No. 712,676, Jun. 10, 1991, Pat. No. 5,210,421.

[51] Int. Cl.⁵ .............................................. G01T 1/166
[52] U.S. Cl. ................................................. 250/363.04
[58] Field of Search ....................... 250/363.04, 363.03, 250/363.1

[56] References Cited

U.S. PATENT DOCUMENTS

| | | | |
|---|---|---|---|
| 4,633,398 | 12/1986 | Gullberg et al. | 364/413.21 |
| 4,670,657 | 6/1987 | Hawman et al. | 250/505.1 |
| 4,692,624 | 9/1987 | Ichihara | 250/363.04 |
| 5,055,687 | 10/1991 | Ichihara | 250/363.09 |
| 5,072,121 | 12/1991 | Jazbec | 250/363.04 |
| 5,210,421 | 5/1993 | Gullberg et al. | 250/363.04 |

FOREIGN PATENT DOCUMENTS

| | | | |
|---|---|---|---|
| 59-79879 | 5/1984 | Japan | 250/363.04 |
| WO91/00048 | 10/1991 | World Int. Prop. O. | |

OTHER PUBLICATIONS

"Attenuation Maps for SPECT Determined Using Cone Beam Transmission Computed Tomography", Manglos et al., *IEEE Transactions on Nuclear Science*, vol. 37, No. 2, Apr. 1990, pp. 600–608.

"Simultaneous Transmission and Emission Scans in Position Emission Tomography", Thompson et al., *IEEE Transactions on Nuclear Science*, vol. 36, No. 1, Feb. 1989, pp. 1011–1016.

"Quantitative SPECT by Attenuation Correction of the Projection Set Using Transmission Data: Evaluation of a Method", Almquist et al., *European Journal of Nuclear Medicine*, (1990), 16:587–594.

"Review of Convergent Beam Tomography in Single (List continued on next page.)

*Attorney, Agent, or Firm*—Fay, Sharpe, Beall, Fagan, Minnich & McKee
*Primary Examiner*—Constantine Hannaher

[57] ABSTRACT

A SPECT system includes three gamma camera heads (22a), (22b), (22c) which are mounted to a gantry (20) for rotation about a subject (12). The subject is injected with a source of emission radiation, which emission radiation is received by the camera heads. Transmission radiation from a transmission radiation source (30) is truncated to pass through a central portion of the subject but not peripheral portions and is received by one of the camera heads (22a) concurrently with the emission data. As the heads and radiation source rotate, the transmitted radiation passes through different parts or none of the peripheral portions at different angular orientations. An ultrasonic range arranger (152) measures an actual periphery of the subject. Attenuation properties of the subject are determined by reconstructing (90″) the transmission data using an iterative approximation technique and the measured actual subject periphery. The actual periphery is used in the reconstruction process to reduce artifacts attributable to radiation truncation and the associated incomplete sampling of the peripheral portions. An emission reconstruction processor (112) reconstructs the emission projection data and attenuation properties into an attenuation corrected distribution of emission radiation sources in the subject.

25 Claims, 9 Drawing Sheets

OTHER PUBLICATIONS

Photon Emission Computed Tomography", Gullberg et al., *Phys. Med. Biol.*, 1992, vol. 37, No. 3, pp. 507–534.

"Boundary Determination Methods for Attenuation Correction in Single Photon Emission Computed Tomography", Gullberg et al., *Emission Computed Tomography: Currents Trends*, P. D. Esser, ed., SMRM, 1983, pp. 33–53.

"An Attenuated Projector-Backprojector for Iterative SPECT Reconstruction", Gullberg et al., *Phys. Med. Biol.*, 30:799–816, 1985.

Advertising Brochure for RPS–400A of Migatron Corporation, 1990, pp. 49–50.

"Maximum Likelihood Reconstruction for Emission Tomography", Shepp et al., *IEEE Trans. Med. Imaging*, MI-1:113–122, 1982.

"EM Reconstruction Algorithms for Emission and Transmission Tomography", Lang et al., *J. Comp. Assist. Tomogr.*, 8:306–316, 1984.

"Whole-Body Single-Photon Emission Computed Tomography Using Dual, Large-Field-Of-View Scintillation Cameras", Jaszczak et al., *Phys. Med. Biol.*, 24:1123–1143, 1979.

"Radionuclide Computed Tomography of the Body Using Routine Radiopharmaceuticals. I. System Characterization", Murphy et al., *J. Nucl. Med.*, 20:102–107, 1979.

"Improved SPECT Using Simultaneous Emission and Transmission Tomography", Bailey et al., *J. Nucl. Med.*, 28:844–851, 1987.

"Comparison of Three Boundary Detection Methods for SPECT Using Compton Scattered Photons", Macey et al., *J. Nucl. Med.*, 29:203–207, 1988.

"SPECT Myocardial Perfusion Imaging Update", Datz et al., *Seminars in Ultrasound, CT, and MR*, vol. 12, No. 1, (Feb.), 1991: pp. 28–44.

"Automated Body Contour Detection in SPECT: Effects on Quantitative Studies", Hosoba et al., *J. Nucl. Med.*, 27:1184–1191, 1986.

"Simultaneous Acquisition of Transmission and Emission Data in TL-201 Cardiac SPECT Using a TC-99m Flood Source", Frey et al., *J. Nucl. Med.*, Abs. No. 379, Proceedings of the 37th Annual Meeting, p. 798.

"Design Possibilities" Advertising Brochure of Nuclear Fields, Inc.

SIMULTANEOUS TRANSMISSION AND EMISSION CONVERGING TOMOGRAPHY

This application is a continuation-in-part of U.S. application Ser. No. 07/712,676, filed Jun. 10, 1991, now U.S. Pat. No. 5,210,421.

BACKGROUND OF THE INVENTION

The present invention relates to the art of diagnostic imaging. It finds particular application in conjunction with single-photon emission computed tomography (SPECT) with multi-headed cameras and will be described with particular reference thereto. It is to be appreciated, however, that the invention will also find application in other non-invasive investigation techniques such as positron emission tomography (PET) and other diagnostic modes in which a subject is examined for emitted radiation.

Heretofore, single photon emission computed tomography has been used to study the radionuclide distribution in subjects. Typically, one or more radiopharmaceuticals were injected into a patient. The radiopharmaceuticals were commonly injected into the patient's blood stream for imaging the circulatory system or for imaging specific organs which absorb the injected radiopharmaceuticals. Gamma or scintillation camera heads were placed closely adjacent to a surface of the patient to monitor and record emitted radiation. In single photon-emission computed tomography, the head was rotated or indexed around the subject to monitor the emitted radiation from a plurality of directions. The monitored radiation data from the multiplicity of directions was reconstructed into a three dimensional image representation of the radiopharmaceutical distribution within the patient.

One of the problems with the SPECT imaging technique is that photon absorption and scatter by portions of the subject between the emitting radionuclide and the camera head distorted the resultant image. One solution for compensating for photon attenuation was to assume uniform photon attenuation throughout the subject. That is, the patient was assumed to be completely homogenous in terms of radiation attenuation with no distinction made for bone, soft tissue, lung, etc. This enabled attenuation estimates to be made based on the surface contour of the subject. Of course, human subjects do not cause uniform radiation attenuation, especially in the chest.

In order to obtain more accurate radiation attenuation measurements, a direct measurement was made using transmission computed tomography techniques. That is, radiation was projected from a radiation source to the patient and radiation that was not attenuated was received by detectors at the opposite side. The source and detectors were rotated to collect data through a multiplicity of angles. This data was reconstructed into an image representation using conventional tomography algorithms. The radiation attenuation properties of the subject from the transmission computed tomography image were used to correct for radiation attenuation in a later SPECT or other emission study.

One of the problems with this two step technique resided in registering the transmission computed tomography and the SPECT or other emission study images. Any misalignment of the two images provided erroneous radiation attenuation information which impaired the diagnostic value of the reconstructed images. Registration was improved by using discrete extrinsic or intrinsic landmarks that were known to bear a constant relationship to the patient's anatomy during the two studies. Another technique was to use a three dimensional surface identification algorithm to construct numerical models of the external surface of the images. The numerical models were then translated, rotated, and descaled until an optimal match was found. Nonetheless, there was still significant uncertainty when combining images from different modalities. Moreover, inconvenience, cost, and double scan time were inevitable.

To overcome these disadvantages, simultaneous transmission and emission data acquisition was utilized. The gamma camera head was positioned on one surface of the subject and a large plane of a radiation source was disposed opposite the camera head, e.g. between the subject and a counterweight for the camera head. The patient was injected with a different radionuclide from the radionuclide in the large planar source. Using conventional dual radionuclide technology, the data from the injected or emitted radionuclide and the data from the larger planar source or transmitted radiation were separated. The transmitted data was reconstructed using parallel ray transmitted computed tomography algorithms to produce attenuation correction coefficients for use in the emitted radiation reconstruction.

One problem with using a large planar source resided in its large bulk and weight. The large size of the planar source prevented the use of systems with multiple gamma cameras. Another drawback was the poor counting statistics of parallel-beam geometry reconstructions. Stronger radiation sources could be utilized to compensate for the poor counting statistics, but the associated higher patient radiation exposures are undesirable.

The present invention contemplates a new and improved simultaneous transmission and emission tomography method and apparatus which overcomes the above-referenced problems and others.

SUMMARY OF THE INVENTION

In accordance with one aspect of the present invention, a method is provided for determining an emission source distribution within a subject. Radiation photons are transmitted through the subject from a multiplicity of angular positions. Transmission radiation photons are detected from a plurality of angular positions around the subject. Transmission radiation photons which have passed through a central region of the subject are received at the multiplicity of angular positions. Transmission radiation photons which have passed through edge portions of the subject as well are detected at some of the angular positions. Radiation photons which have passed through at least some of the edge portions are not detected at some of the angular positions around the subject. Radiation attenuation coefficients are determined from the detected transmission radiation photons. In this manner, the radiation attenuation coefficients contain artifacts attributable to detection of transmission radiation photons which have traversed parts of the subject edge portions at only some angular positions and not at others. Weighting factors are determined from the artifact containing attenuation coefficients. Emission radiation photons emitted by the emission sources distributed in at least the central portion of the subject are detected. From the detected emission radiation photons and the weighting factors, an attenuation corrected representation of the emission source distribution in the subject is reconstructed.

In accordance with another aspect of the present invention, an actual periphery of the subject is measured, preferably by ultrasonic ranging. The determined actual periphery of the subject is used in conjunction with determining the radiation coefficients from the detected transmission photons.

In accordance with another aspect of the present invention, a method is provided of determining an emission source distribution within a subject. A beam of radiation is transmitted through the subject. The beam is truncated such that at least one effective dimension of the beam is smaller than a maximum cross-sectional dimension of the subject. At a plurality of angular orientations around the subject, transmission radiation which has passed through a central portion of the subject is detected. Due to the beam truncation, no transmission radiation passing through edge portions of the subject are detected at some angles. An actual periphery of the subject is measured. From the detected transmission radiation and the measured actual subject periphery, radiation attenuation properties of the subject are determined. Radiation emission photons emitted by emission sources distributed within the central and edge portions of the subject are detected. From the detected emission radiation photons and the determined attenuation properties of the subject, an attenuation corrected representation of the emission source distribution in the subject is reconstructed.

In accordance with another aspect of the present invention, the gamma camera system is provided. A plurality of gamma camera heads face an examination region for receiving emission radiation from a subject in the examination region. A transmission radiation source is disposed across the examination region opposite a first of the heads. A circumferential moving means moves the heads and the transmission radiation source circumferentially around the examination region. A collimating means collimates the emission and transmission radiation received by at least the first head such that at least some circumferential orientations around the examination region, the first head receives transmission radiation from only a portion of the subject and at other circumferential orientations around the examination region, the first head receives transmission radiation from a larger portion of the subject. A first reconstruction means reconstructs received transmission radiation data from at least the first head to generate an indication of radiation attenuation properties of the subject. The radiation attenuation properties tend to include artifacts attributable to the collection of transmission radiation data which is passed through different portions of the subject at different circumferential orientations. A second reconstruction means processes emission radiation data from the heads and the artifacted attenuation properties to generate an attenuation corrected representation of emission radiation distribution in the examination region.

One advantage of the present invention is that it accurately and efficiently produces attenuation corrected emission radiation data reconstruction.

Another advantage of the present invention is that it concurrently collects the emission data and the transmission correction data.

Another advantage of the present invention is that it accurately corrects emission data with projection data from a truncated transmission source which transmission data has artifacts attributable to the truncation.

Still further advantages will become apparent to those of ordinary skill in the art upon reading and understanding the following detailed description.

BRIEF DESCRIPTION OF THE DRAWINGS

The invention may take form in various steps and arrangements of steps and in various components and arrangements of components. The drawings are only for purposes of illustrating the preferred embodiment and are not to be construed as limiting the invention.

DETAILED DESCRIPTION OF THE PREFERRED EMBODIMENT

Figure 1:
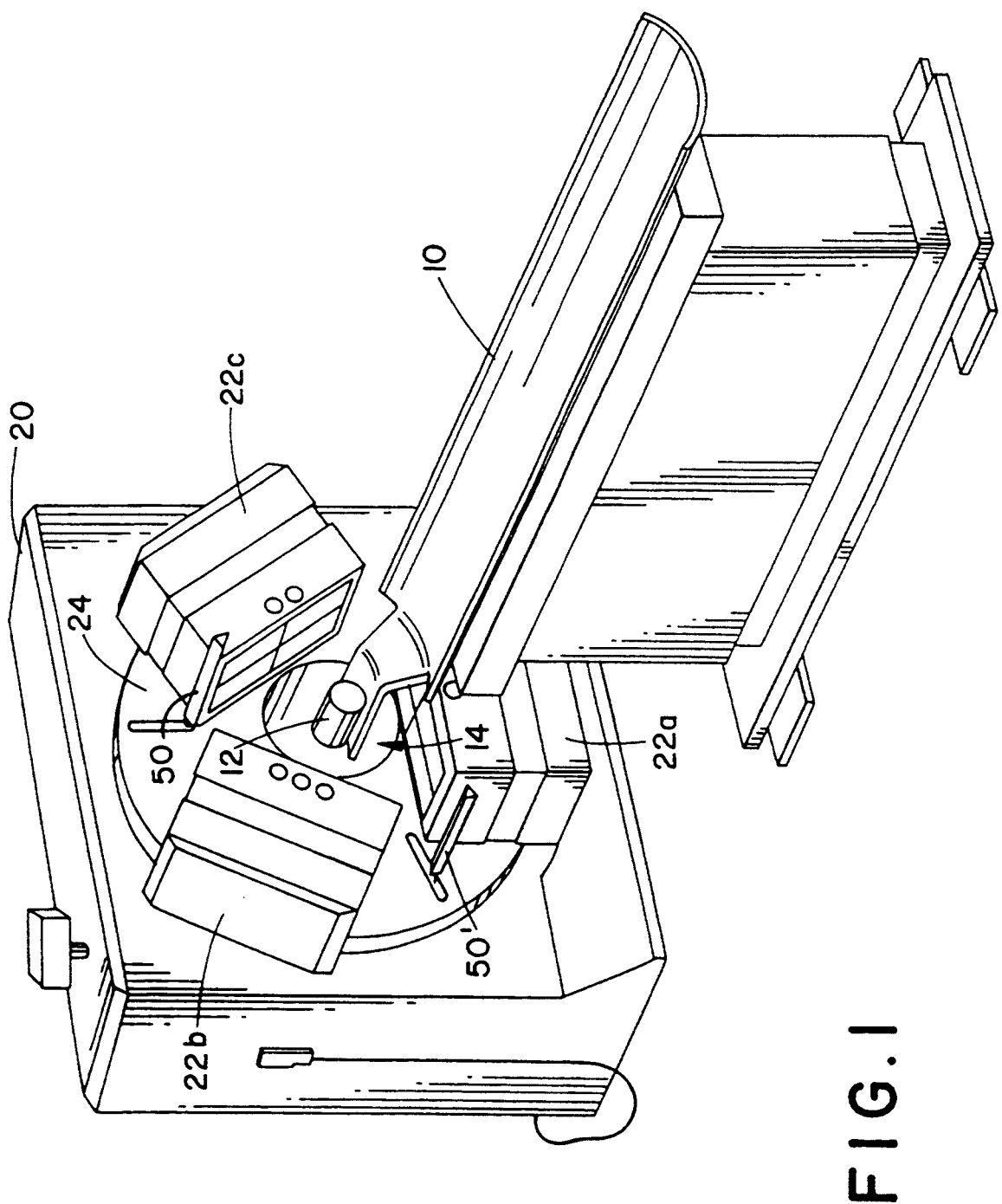
FIG. 1 is a prospective view of a gamma camera system in accordance with the present invention.

With reference to FIG. 1, a SPECT camera assembly includes a patient couch or support means 10 for holding a subject such as a phantom 12 or a human patient in an examination region 14.

Figure 2:
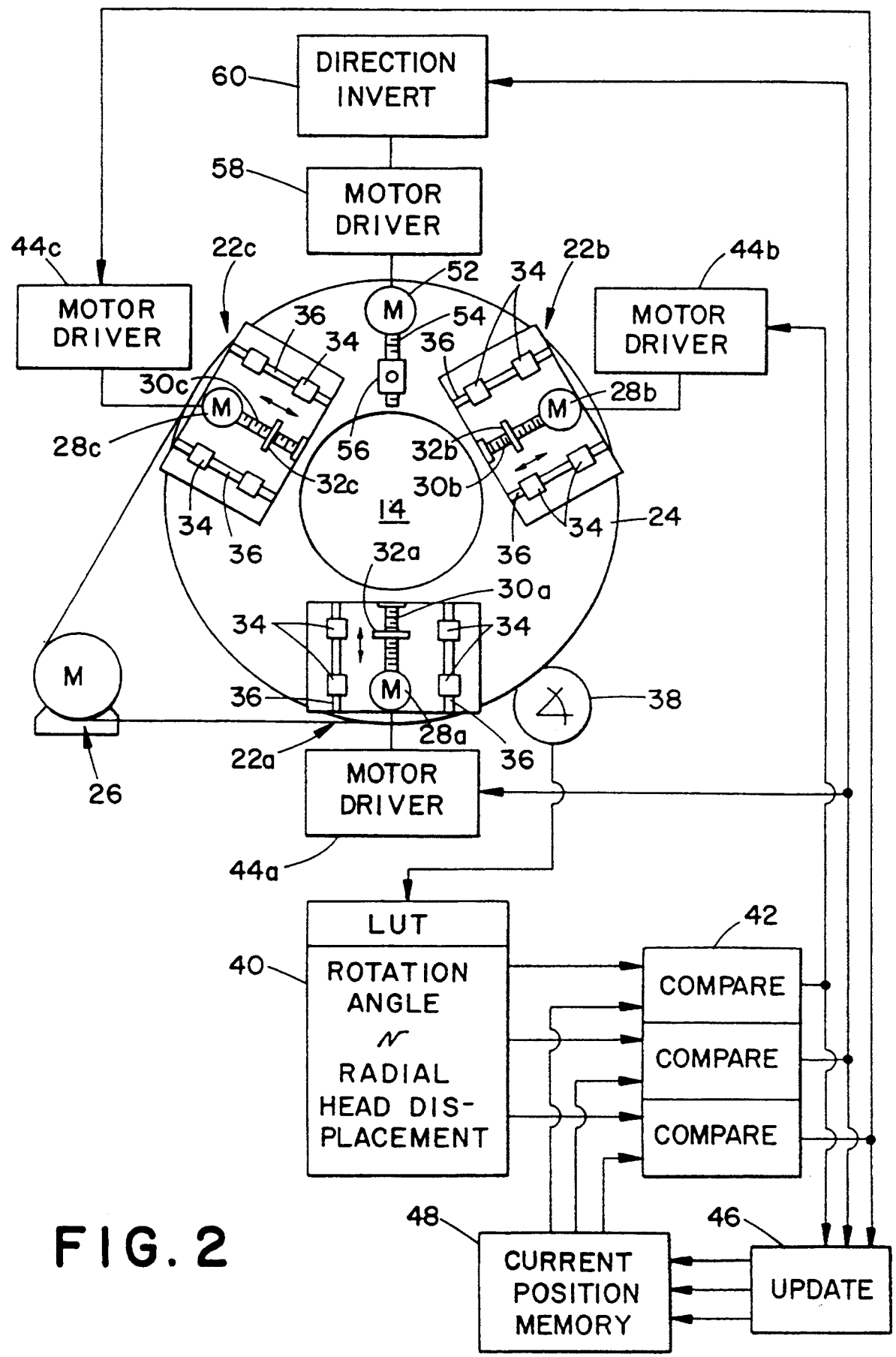
FIG. 2 is a diagrammatic view of a gamma camera head and transmission source position controller.

With continuing reference to FIG. 1 and further reference to FIG. 2, a gantry 20 supports a plurality of gamma camera heads 22a, 22b, and 22c at regular intervals around the examination region 14, e.g. 120°. More specifically, a rotating means including a rotating drum or face plate 24 to which the camera heads are mounted and a drive motor 26 selectively rotate the camera heads around the examination region. Linear drive means, such as motors 28a, 28b, 28c that rotate screw driver 30a, 30b, 30c, that engage followers 32a, 32b, 32c, are mounted on the reverse side of the face plate for selectively moving each gamma camera head on roller carriages 34a along tracks or guides 36 radially toward and away from the subject.

A control means is provided for rotating the camera heads around the subject and moving the camera heads toward and away from the subject during the rotation, as is conventional in the art. More specifically, an angular position detector 38 detects the number of degrees of rotation of the plate 24 from an arbitrary 0° origin. A look-up table 40 is loaded with one of a plurality of selectable orbits e.g. an oval orbit of a preselected size which most closely matches the patients size. The look-up table 40 is addressed by the monitored angle to retrieve the radial distance from the center of the examination region for each camera head at that angle. A comparing means 42 compares the desired radial distance from the look-up table with the actual, current radial distance of each head. The difference is conveyed to drivers 44a, 44b, 44c which cause corresponding linear motors 28a, 28b, 28c to move the heads the corresponding physical distance. A memory update means 46 add/subtracts the distance differences with the corresponding radial position of each head in a current position memory 48. This enables the camera heads to move around the subject in a circular path, an elliptical path, a peanut-shaped path, or other orbits by merely reloading the look-up table 40 from a large memory, such as a disc (not shown), of precalculated orbits. The symmetry in a circular path facilitates reconstruction of the collected data; whereas, the elliptical and peanut orbits move the gamma camera heads closer to the patient improving image quality.

A radiation source 50, a line source in the FIG. 1 embodiment, is mounted directly opposite a first of the gamma camera heads 22a and between the other two gamma camera heads 22b, 22c. The radiation source is selectively positionable radially either closer to or further from the first camera head 22a. Preferably, the radiation source is disposed behind a plane of the face of the camera heads 22b and 22c such that radiation therefrom cannot impinge directly on the other camera heads 22b, 22c. A collimating or shield means 51 is mounted to the radiation source to limit the projection of radiation to a fan beam that intercepts the first gamma camera head 22a. Optionally, one or more additional radiation sources 50' may also be provided. The transmission radiation source may be a tube or vessel filled with a radionuclide or an active radiation generator such as an x-ray tube.

A motor 52 rotates a screw 54 that moves a follower 56 which is mounted to move the radiation source radially. Preferably the control circuit controls the motor 52 such that the radiation source 50 and the first camera head 22a stay a fixed distance apart. Direction invertor means 60 reverses the sign or direction of movement such that a driver 58 causes the motor 52 to move the radiation source the same distance, but in the opposite radial direction relative to the center of the examination region as the driver 44a causes the motor 28a to move the first head 22a. Alternately, the transmission radiation source 50 may be mounted to one of the adjoining heads 22b or 22c. Because movement of either head radially changes the effective angle of the fan, the reconstruction algorithm is adjusted with angular position to accommodate the changing effective fan angle. The effective fan angle is preferably precalculated and stored in the look-up table 40.

As is conventional in the art, each camera head has a scintillation crystal that responds to incident radiation by producing a flash of light. An array of photomultiplier tubes produce electrical signals in response to each flash of light. The signals responsive to the same scintillation or flash of light are combined. The magnitude of the resultant sum is indicative of the energy of the incident radiation and the relative response of the closest photo-multiplier tubes is indicative of the spatial location of the scintillation.

Figure 3:
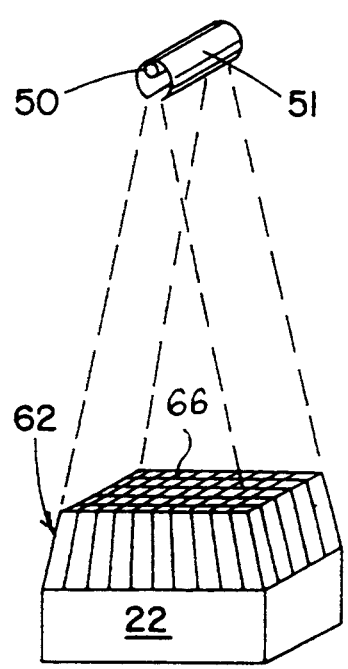
FIG. 3 is a diagrammatic illustration of a line source, gamma camera head, and fan beam collimator.
Figures 4A, 4B:
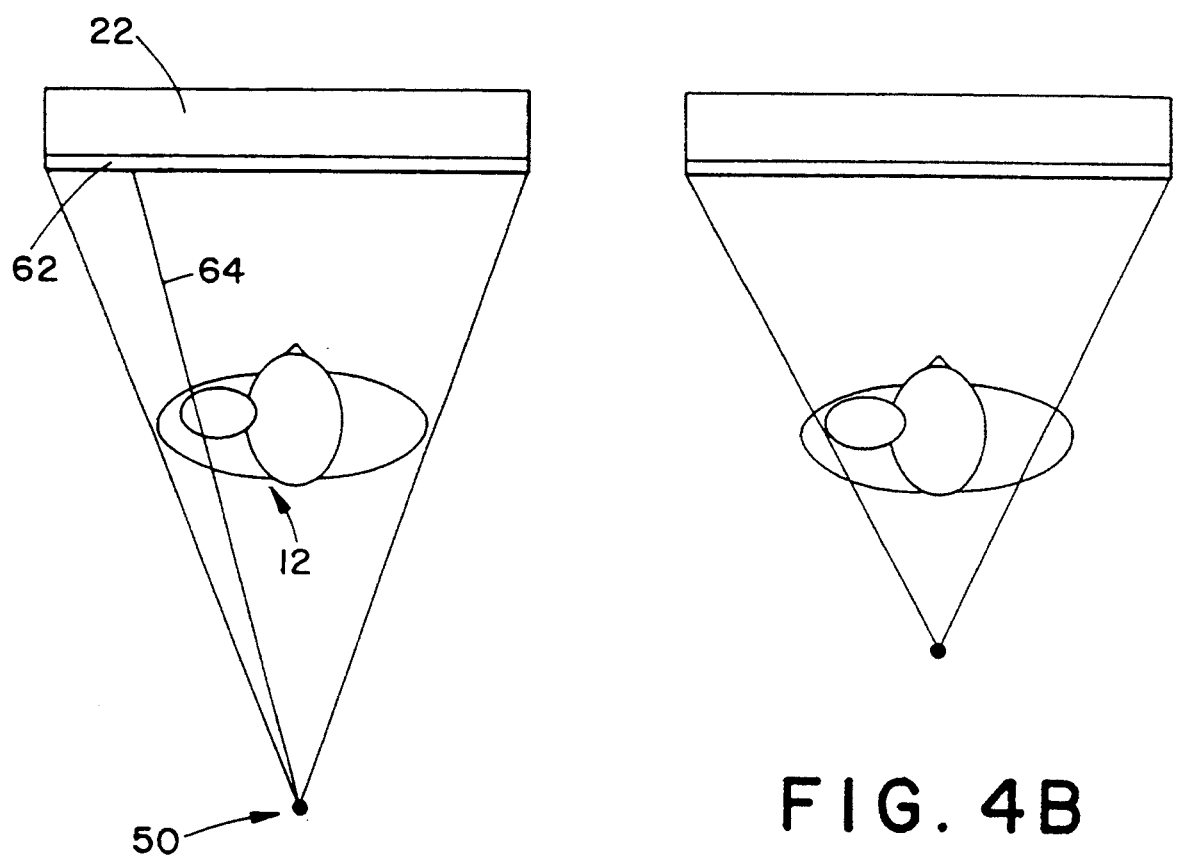
FIGS. 4A and 4B are diagrammatic illustrations of a non-truncated and a truncated transmission scan.

With reference to FIG. 3, collimator 62, limit each incremental area of the scintillation crystal receiving radiation from along a fixed direction or ray, e.g. ray 64 of FIG. 4A. The collimator has a plurality of vanes 66 which are directed toward a focal point, typically the transmission radiation source 50. The vanes are sufficiently long that radiation impinging on the corresponding detector head is limited to radiation coming along a ray substantially from the focal point. In a preferred embodiment, the focal point and head size are selected such that a patient or subject under examination is completely encompassed within the transmission radiation fan as illustrated in FIG. 4A.

Conventional gamma camera heads can image radiation in two or more energy windows or ranges simultaneously. In a conventional dual energy gamma camera head, the sum signals are sorted based on amplitude. More specifically, energy windows or ranges are defined. Each window corresponds to a photopeak or energy spectrum of a radionuclide to be used in the examination. In the preferred embodiment, the injected or emission radionuclide has one preselected energy and the radiation source 50 or transmissive radiation has a second different energy. In this manner, the camera heads separate the transmission and emission radiation data by using the conventional energy separation circuitry used during dual injected radiopharmaceutical examinations. A position resolver resolves the position on the crystal, hence the ray angle, corresponding to scintillations or radiation events within one of the energy windows.

Figure 5:
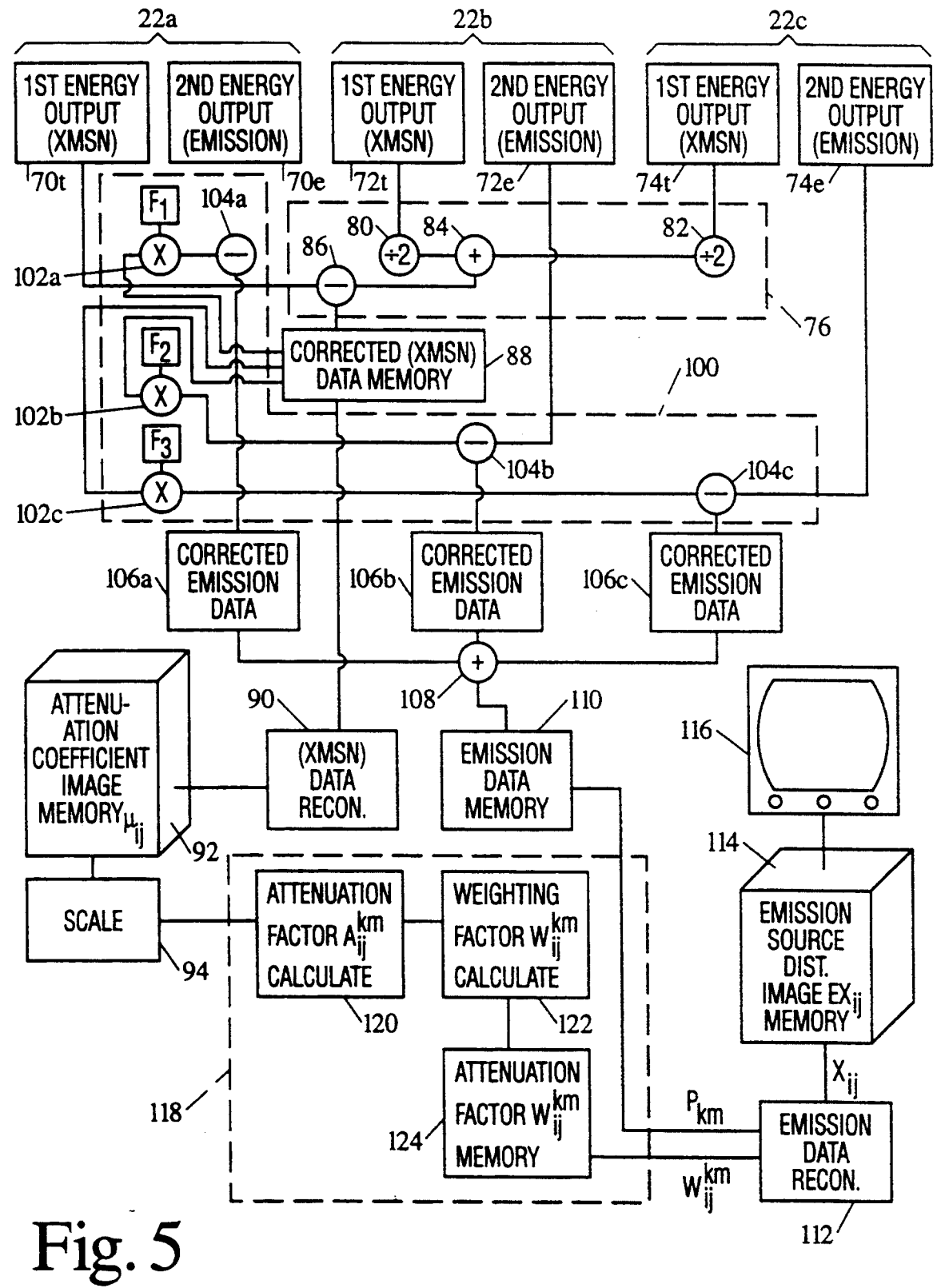
FIG. 5 illustrates the technique for processing the emission and transmission data in different energy ranges collected with the camera system of FIG. 1.

With reference to FIG. 5, the first head 22a has first energy level output means 70t for separating and outputting location or ray signals for each scintillation with an energy in the range of the transmission source 50 and a second energy level output means 70e for separating and outputting location or ray signals for each scintillation in the energy range of the emission radionuclide. Although the second head 22b and the third head 22c do not receive the transmission radiation directly, they do receive some of the transmission radiation by scattering and photons from other photopeak(s) of the emission source. Accordingly, the second head 22b has a transmitted energy output means 72t for separating and outputting transmission energy range data and the third head 22c has a transmitted energy output means 74t for transmission energy range data. A transmission radiation data correction means 76 corrects the transmission energy data from the output means 70t for emission radiation photopeak(s) in the transmission energy range.

The transmission radiation correction means 76 includes a pair of dividers 80 and 82 which divide the output signals 72t and 74t in half, respectively. A summing means 84 sums these two half signals to provide a signal which is effectively the average of other emission photopeak photons received by heads 22b and 22c. A subtracting means 86 subtracts the average number of photons from the emission source detected in the transmission energy range by heads 22b and 22c from the transmission energy signals from head 22a. A corrected transmission projection data memory 88 stores the corrected transmission projection data.

A transmission reconstruction means 90 reconstructs the transmission radiation data with a conventional CT or iterative reconstruction algorithm into a three dimensional electronic image representation stored in a three dimensional transmission radiation or attenuation image memory 92, e.g. a fan beam reconstruction algorithm. Each pixel or voxel of the attenuation image memory 92 represents the radiation attenuation by a corresponding pixel or voxel of the examination region 14 or the subject being examined. Thus, when an emission radiation event occurs at a given pixel or voxel, one can determine the amount of radiation attenuation along the rays between the event voxel and the points on each head at which the scintillation occurs by summing the attenuation values of each pixel or voxel through which the ray passes. The attenuation probability of detection is the exponentiation of the negative of this sum. A further correction can be made by determining the distance through each intervening pixel or voxel the ray passes. When the ray extends through a pixel or voxel squarely from one face to the opposite face, the entire attenuation value is added. If the path goes through only a small corner, a correspondingly smaller portion of the attenuation value is added. A scaling means 94 adjusts the attenuation data in accordance with the relative energy of the transmission and emission sources, e.g. the ratio or a non-linear relationship of energy.

A major goal in transmission CT is to compute local attenuation coefficients for the object of interest. In the preferred embodiment, the recorded projection data in a transmission scan is converted to an appropriate form by taking the natural logarithm of the ratio of unattenuated acquired count per pixel or voxel (flood image $N_0$) to observed count at a given pixel (recorded projection N). Other algorithms, as illustrated in "EM Reconstructions for Emission and Transmission Tomography", Lang and Carson, J. Comp. Assist. Tomogr., vol. 8, pp. 306–316 (1984), do not require an initial determination of the logarithm. For those regions with observed count greater than the flood image, the line integral of the attenuation coefficients is set equal to zero, i.e.:

$$N = N_0 e^{-\mu x} \tag{1a}$$

$$\text{projection} = \int \mu dx = \ln\left(\frac{N_0}{N}\right) \text{ if } N \leq N_0 \tag{1b}$$

$$\text{projection} = 0 \text{ if } N > N_0 \tag{1c}$$

After performing this conversion, a conventional CT or iterative reconstruction algorithm is used to obtain the map of attenuation coefficients $\mu_{ij}$. The calculated attenuation map is used to correct for the photon attenuation in the emission study.

By way of a specific example of the scaling means 94 in which scales the attenuation coefficients $\mu^{Tl}_{ij}$ of a 75 keV Tl-201 emission source relative to the attenuation coefficients $\mu^{Tc}_{ij}$ of a 140 keV Tc-99m transmission source, the attenuation coefficients $\mu^{Tl}_{ij}$ for Tl-201 emission is approximated by:

$$\mu^{Tl}_{ij} = \frac{\mu_{75kev}}{\mu_{140kev}} \times \mu^{Tc}_{ij} = \frac{0.184/\text{cm}}{0.153/\text{cm}} \times \mu^{Tc}_{ij} = 1.2 \mu^{Tc}_{ij}. \tag{2}$$

Another scaling method is applied to the higher energy (140 keV) attenuation map. This method uses a look-up table of the linear attenuation coefficients for different materials at both 75 keV and 140 keV. A data interpolation technique is used to determine the scaling factor to transform the attenuation distribution at 140 keV to that at 75 keV.

The second head similarly has an emission energy location or ray signal output means 72e and the third head 22c has an emission energy ray signal output 74e. Some of the transmission photons and scattered emission photons are detected within the emission radiation energy range. An emission radiation correction means 100 removes the component of the measured emission radiation which is attributable to the transmission radiation. The emission radiation correcting means 100 includes a first multiplying means 102a for multiplying the corrected first detector head transmission radiation signal from memory 88 by a scaling factor $F_1$. A second multiplying means 102b multiplies the corrected transmission radiation signal corresponding to the first detector head from the corrected transmission data memory 88 by a second scaling factor $F_2$ and a third multiplying means 102c multiplies the corrected transmission signal from the memory 88 by a third scaling factor $F_3$.

The scaling factors $F_1$, $F_2$, $F_3$ are determined from initial calibration tests. The tests begin with collecting pure transmission data using a cold phantom, i.e. no emission source. The correction factors $F_1$, $F_2$, $F_3$ are determined for each head by calculating a ratio of the counts in the emission and transmission energy windows or ranges. Subtraction circuits 104a, 104b, 104c subtract the product of the transmission radiation value and the corresponding correction factor from the actual measured emission radiation projection data. Corrected emission ray or location signal memories 106a, 106b, and 106c store the corrected emission projection data from heads 22a, 22b, 22c, respectively. A combining circuit 108 combines the corrected emission data from heads 22a, 22b, and 22c. More specifically, the combining circuitry combines data from each head representing the same ray. That is, the collimator 62 defines the path, relative to the head, along which radiation travelled to cause scintillation at the monitored location on the head. The location on the head and the angle of the head when the event was monitored define the ray or path between the corresponding emission source and the point of receipt.

The corrected emission projection data from the combining means 108 is stored in a total emission projection data memory 110. An emission data reconstruction processor 112 reconstructs the emission data into a corresponding three dimensional image representation which is stored in an emission image memory 114. A video display terminal 116 or other display means provides a man-readable display of the reconstructed emission distribution. Typically, various displays will be selected, such as transverse or lateral slices through the patient, or even a three dimensional prospective representation. An attenuation correction means 118 corrects the emission data $P_{km}$ from total emission projection data memory 110 for attenuation by iterative reconstruction algorithms or means and provides corrected emission projection data to the emission data reconstruction means.

Stated more mathematically, the emission projection data $P_{km}$ at projection angle $\Theta_m$ and detector bin or ray k, and the image or back projection value $X_{ij}$ at pixel (i,j) are defined as:

$$P_{km} = \sum_{i,j} W^{km}_{ij} X_{ij}, \tag{3a}$$

-continued $$X_{ij} = \sum_{k,m} W_{ij}^{km} P_{km},\qquad(3b)$$

where the weighting factor $W^{km}_{ij}$ is given by $$W_{km}^{ij} = \frac{A_{ij}^{km}}{\mu_{ij}}(1 - e^{\mu_{ij}l_{ij}^{km}}) \text{ if } \mu_{ij} > 0.\qquad(3c)$$

$$W_{ij}^{km} = l_{ij}^{km} A_{ij}^{km},\ if\ \mu_{ij}=0\qquad(3d),$$

where $l^{km}_{ij}$ is the length of the ray through the pixel. The attenuation factor $A^{km}_{ij}$ (see Equation (6)) is the exponential of the line integral of the attenuation coefficients $\mu_{ij}$ from $b_{ij}$, the entry point of projection ray to the pixel (i,j), to the detector. If no attenuation correction is needed, the attenuation coefficients $\mu_{ij}$ are set to be zero.

More specifically, the attenuation correction means 118 includes an attenuation factor calculating means 120 which calculates the attenuation factors $A^{km}_{ij}$. The attenuation factor calculating means calculates the exponential of the line integral of the scaled attenuation coefficients $\mu_{ij}$ along each ray k at angle $\Theta_m$ between pixel (i,j) and the detector head. Of course, zero values for rays that do not intersect the pixel need not be stored.

A weighting factor calculating means 122 calculates the weighting factors $W^{km}_{ij}$ in accordance with Equation (3c) for each emission data ray k and angle $\Theta_m$ and each pixel (i,j) of the emission distribution image memory 114. The calculated weighting factors are stored in an attenuation weighting factor memory or look-up table 124. The emission data reconstruction means 112 performs the multiplication and summing of Equation (3b) to generate the image values $X_{ij}$ at each iteration in accordance with the iterative scheme of Equation (4).

As in most reconstruction schemes, the subject region is divided into small pixels. For each pixel, an emission radionuclide concentration and a projection radiation attenuation coefficient are determined. These parameters can be estimated by maximizing the likelihood (probability of observations). The preferred algorithm includes a technique for computing maximum likelihood estimates. This algorithm has the unique ability to model the Poisson nature of photon counting and the physical differences between transmission and emission tomography. For SPECT, photon attenuation and variation of resolution with depth can be treated appropriately and the use of an accurate statistical model can improve the quality of reconstruction with low counts. The combination of good statistical and physical models should produce superior reconstructions. The preferred algorithm which the emission data reconstruction means 112 performs the EM iterative reconstruction algorithm, i.e.:

$$X_{ij}^{n+1} = \frac{X_{ij}^n}{\sum_{k',m'} W_{ij}^{k'm'}} \sum_{k,m} \left[ W_{ij}^{km} \frac{P_{km}}{P_{km}^n} \right].\qquad(4)$$

Figure 6:
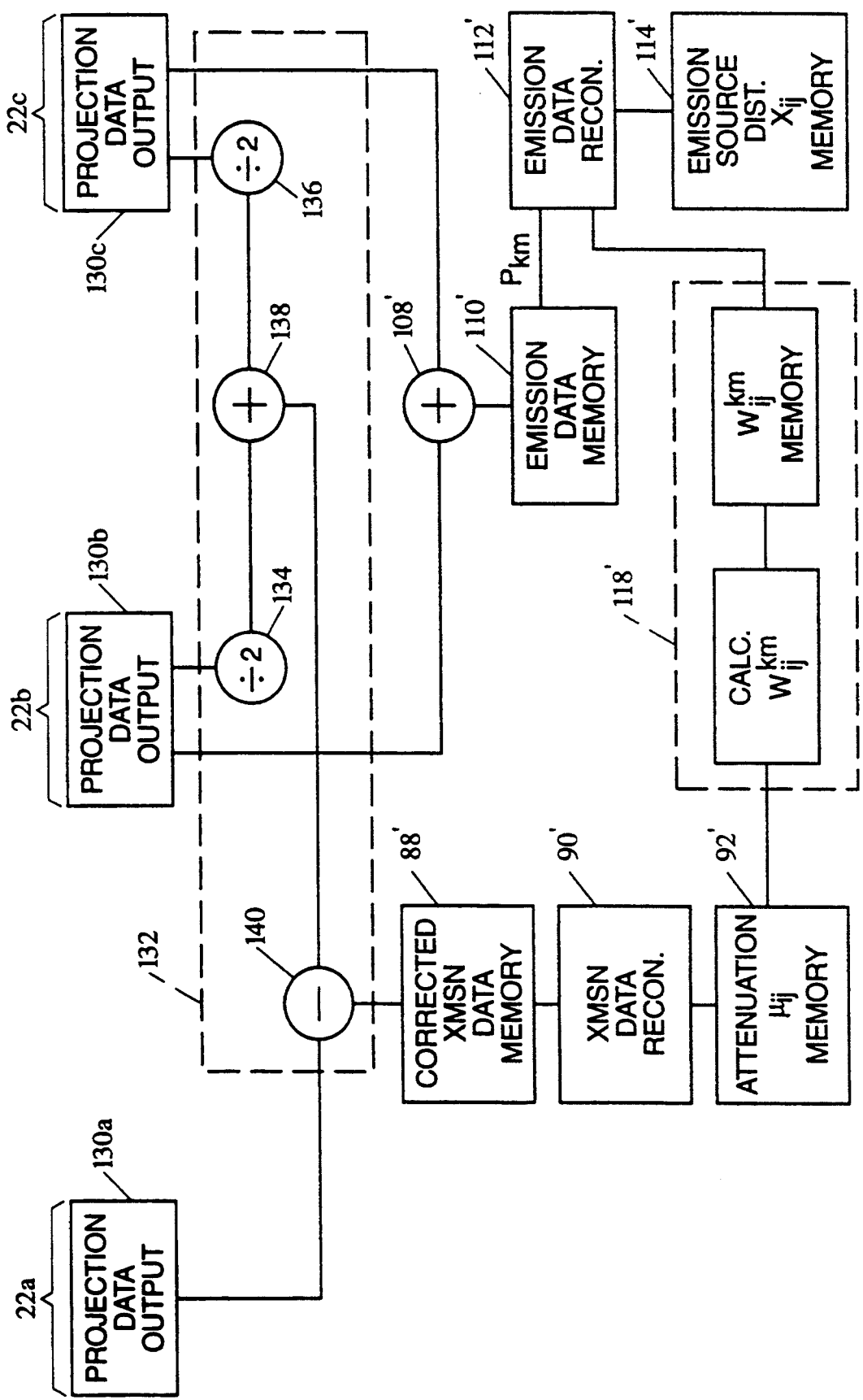
FIG. 6 illustrates the technique for processing emission and transmission data in the same energy range collected with the camera system of FIG. 1.

With reference to FIG. 6, the emission and transmission radiation may be sensed with the same energy range or window. Head 22a receives both the transmission and emission radiation; whereas, heads 22b and 22c receive the emission radiation. The heads 22a, 22b, and 22c have outputs 130a, 130b, and 130c, respectively, for outputting the common energy range radiation data. A transmission data correction means 132 corrects the data from output 130a in accordance with each emission data output from detector head outputs 130b and 130c. More specifically, the transmission data correcting means includes dividers 134 and 136 which divide the data from outputs 130b and 130c in half and an adding means 138 which combines the two halves to generate an average of the data received by the second and third heads. A subtraction means 140 subtracts the average data received by the second and third heads from the data received by the first head 22a to generate corrected transmission projection data which is stored in a corrected transmission data memory means 88'. A transmission data reconstruction means 90' reconstructs the corrected transmission data from the corrected data transmission memory means 88' to generate attenuation image data which is stored in an attenuation image memory means 92'.

An emission data combining means 108' combines emission data from the second and third heads and stores the emission data in an emission data memory means 110'. An attenuation correction means 118' corrects the emission data in accordance with the attenuation data as described above in conjunction with the two energy embodiment. An emission data reconstruction means 112' reconstructs the corrected emission data to generate an emission source distribution image which is stored in an emission source distribution memory means 114'.

With reference to FIG. 4B, more accurate gamma camera images can be reconstructed when the collimators focus on the region of interest to be imaged within the subject. Better emission images can be generated by moving the focal point of the collimators closer to the center of the patient. When the transmission radiation source is moved closer to the patient, part of the patient, at some angles, falls outside of the transmission fan, i.e. there is a truncation of part of the subject. The truncated region of the body tends to cause a ring artifact of analogous diameter around the reconstructed image.

One solution is to use different collimators on head 22a, that receives both emission and transmission radiation from heads 22b and 22c which receive only the emission radiation. That is, the emission only heads have collimators with a relatively short focal length, e.g. 50 cm., and the head 22a which receives both transmission and emission radiation has a longer focal length, e.g. 110 cm.

In another solution, the oval cross-section of a human patient which is only moderately truncated provides sufficient data to calculate the attenuation coefficient factors for the EM iterative construction algorithm and analogous algorithms to solve the transmission reconstruction problem as a solution to a system of linear equations. Even though the transmission image is distorted, the attenuation factors $A^{km}_{ij}$ (the exponentiation of the partial line integrals of the attenuation distribution $\mu_{ij}$) are measured accurate enough for those attenuation factors that have the greatest influence from the emission measurements.

Figure 7:
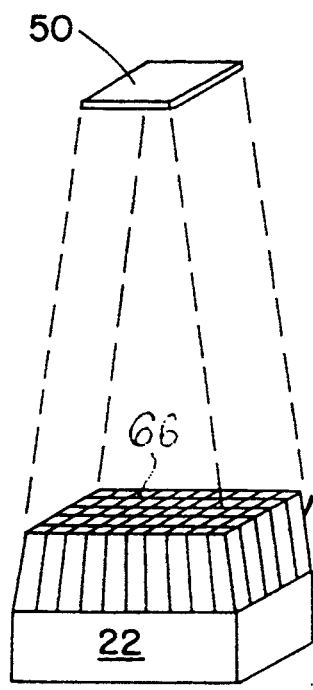
FIG. 7 is a diagrammatic illustration of an alternate embodiment using a rectangular bar transmission radiation source and a fan beam collimator.

With reference to FIG. 7, in an alternate embodiment, the transmission radiation source is a rectangular bar source which projects a fan beam or which is restricted to generate a fan beam of transmitted radiation toward a fan beam collimator mounted on the opposite detector head.

Figure 8:
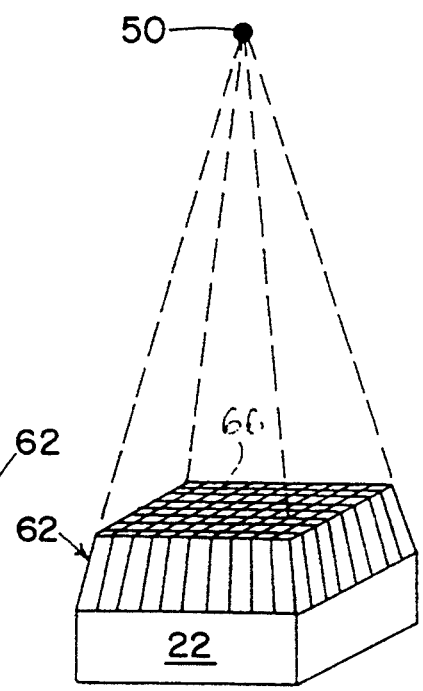
FIG. 8 is a diagrammatic illustration of a point transmission radiation source with a cone beam collimator.

With reference to FIG. 8, in another alternate embodiment, the radiation source is a point source which is restricted to direct a cone or pyramid of transmission radiation toward the oppositely disposed detector head. A cone beam collimator has tunnels which focus to a focal point at some distance from its surface.

Figure 9:
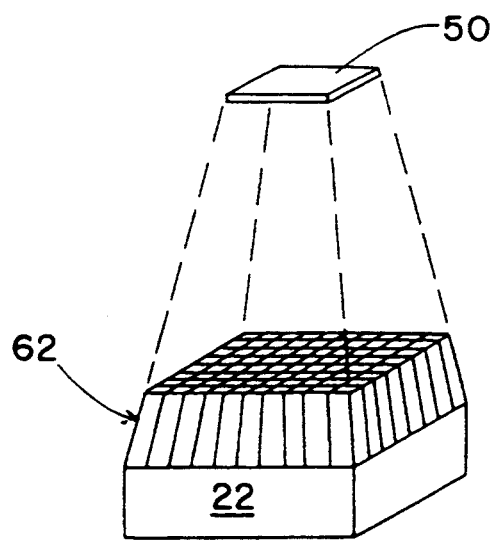
FIG. 9 is a diagrammatic illustration of a disk radiation source with a cone beam collimator.

In the alternate embodiment of FIG. 9, the radiation source is a small flat rectangular source or a disk source and the collimator a cone beam collimator.

Figure 10:
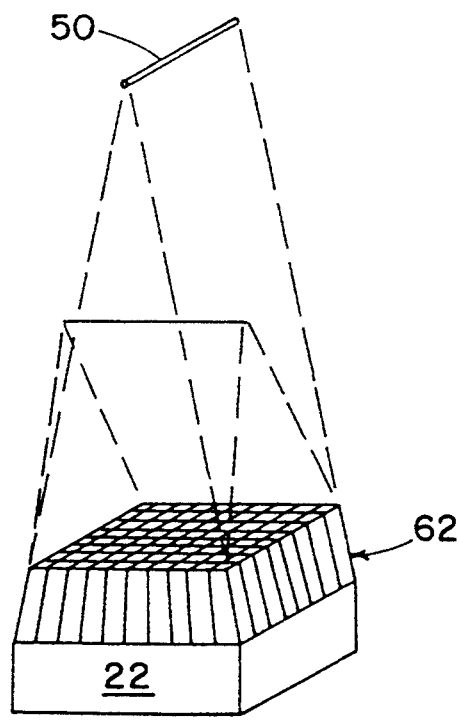
FIG. 10 is a diagrammatic illustration of a line radiation source with an astigmatic collimator.

With reference to FIG. 10, as yet another alternative, the transmission radiation source is a line source and an astigmatic collimator is used which places the focal point at two different focal lines. As yet another alternative, a flood source and a parallel collimator are used.

When imaging a subregion of the human torso with the collimator as illustrated in FIG. 4B, the human body is truncated. In the orientation of FIG. 4B, side edges of the patient torso are not imaged. However, when the source and detector rotate 90°, all portions of the torso are imaged. In this manner, transmission radiation which passes through the region of interest is collected in all orientations, but transmitted radiation which passes through truncated regions of the subject's torso are collected at only some angles.

Figure 11:
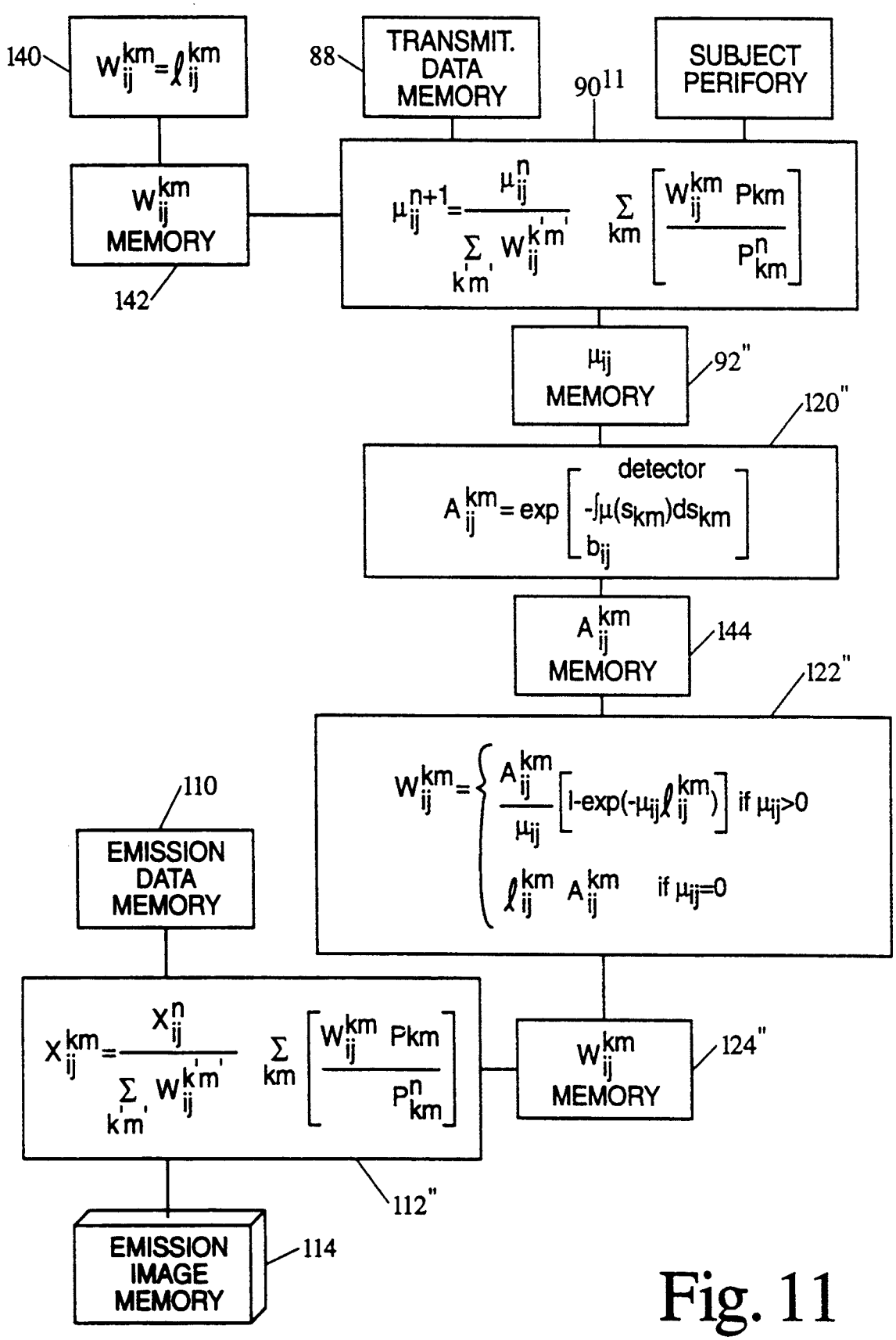
FIG. 11 illustrates a technique for processing truncated transmission and emission data.

With reference to FIG. 11, the transmission data 88 is reconstructed to generate the attenuation line integrals, hence the attenuation coefficient $\mu_{ij}$. Due to the truncation, the reconstructed image has artifact errors. However, using the following process, it has been found that the calculated attenuation factors are still usable to correct the emission data 110 to achieve greater accuracy. More specifically, for each angle, a correction means generator 140 approximates the transmission reconstruction weighting factors $W^{km}_{ij}$ by the value $l^{km}_{ij}$ and stores the weighting factors in a table or memory means 142. As described above in conjunction with FIG. 3, $l^{km}_{ij}$ is the length of the ray which impinges on detector coordinate (k,m) through each pixel in (i,j) space. A transmission data reconstruction means 90'' uses an iterative expectation maximization algorithm, or other algorithms such as proposed by Lang and Carson, to reconstruct images from the transmission data 88. More specifically, each attenuation coefficient $\mu_{ij}$ is calculated using the weighting factor $W_{ij}$ from the memory means 142 as follows:

$$\mu_{ij}^{n+1} = \frac{\mu_{ij}^n}{\sum_{k',m'} W_{ij}^{k'm'}} \sum_{k,m} \left[ W_{ij}^{km} \frac{P_{km}}{P_{km}^n} \right]. \tag{5}$$

This, of course, is the same iterative reconstruction algorithm used with the emission data in the embodiments of FIGS. 5 and 6 in Equation (4). With the reconstruction means 90'', a full matrix of the transverse image attenuation coefficients $\mu_{ij}$ is generated and stored in table 92''. From the $\mu_{ij}$ attenuation coefficients table, a means 120'' calculates the attenuation factors $A^{km}_{ij}$. Each attenuation factor is the exponential of the line integral of the attenuation from the point $b_{ij}$ to the detector as described above, i.e.

$$A_{ij}^{km} = \exp\left[ -\int_{b_{ij}}^{detector} \mu(s_{km}) ds_{km} \right], \tag{6}$$

where $b_{ij}$ as defined above is the entry point of the projection ray through pixel (i,j) to the detector and $s_{km}$ is the length along the projection ray. A table of attenuation factors $A^{km}_{ij}$ 144 is thus loaded.

The weighting factors $W^{km}_{ij}$ for the emission data reconstruction are calculated 122'' in accordance with Equations (3c) and (3d) above to load a weighting factor memory means 124'' with the emission reconstruction weighting factors $W^{km}_{ij}$.

An emission data reconstruction means 112'' reconstructs the image data from an emission data memory 110. More specifically, the emission data reconstruction means 112'' uses iterative expectation maximization for maximum likelihood estimates analogous to means 90''. That is, the reconstruction means 112'' calculates each emission data pixel value $x_{ij}$ based on iterative expectation maximization in accordance with Equation (4). The reconstructed emission source pixels $x_{ij}$ are stored in an emission source distribution memory means 114''.

Figure 12:
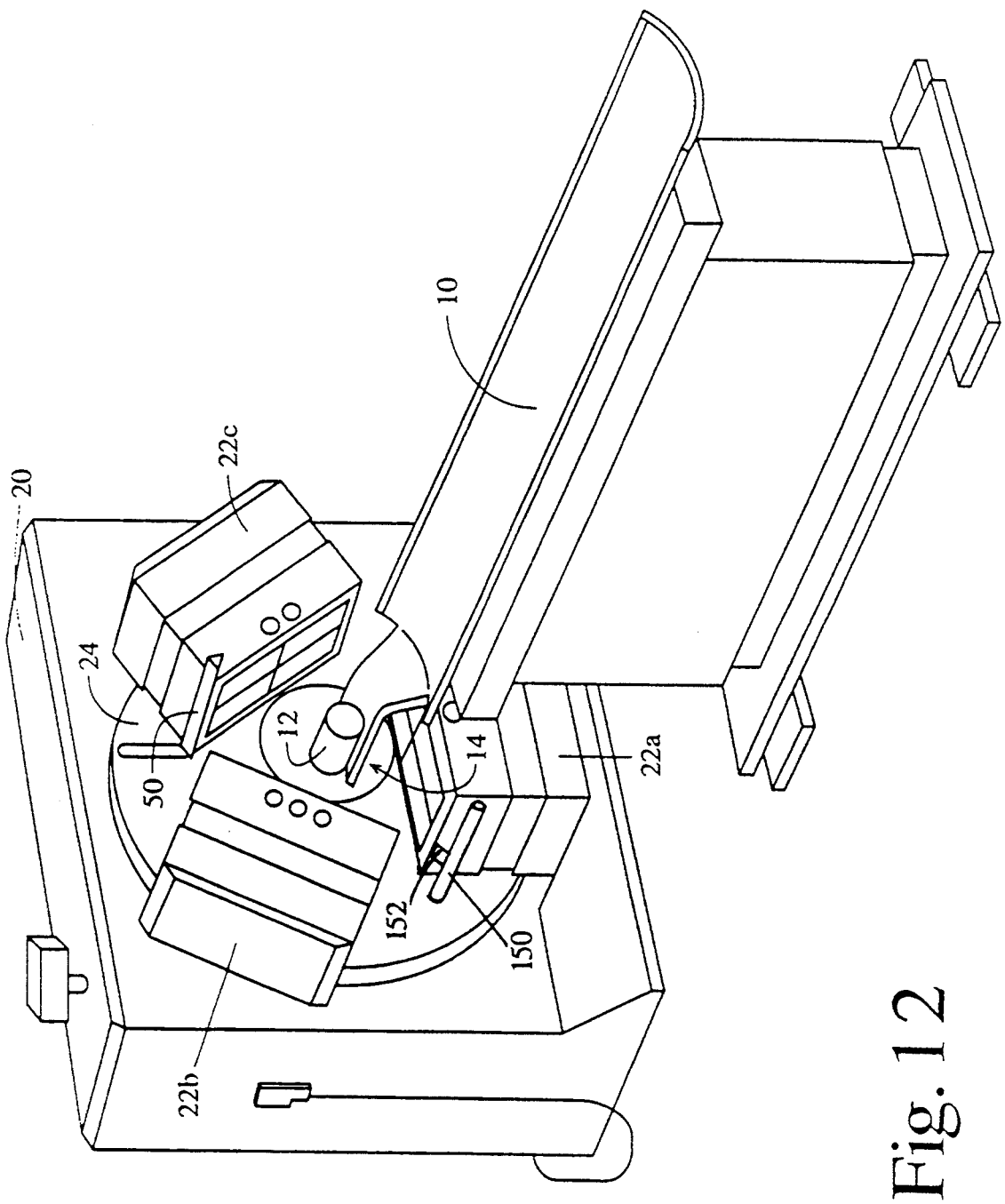
FIG. 12 is a diagrammatic illustration of an alternate embodiment of the gamma camera system of FIG. 1 including a means for measuring subject contour.
Figure 13:
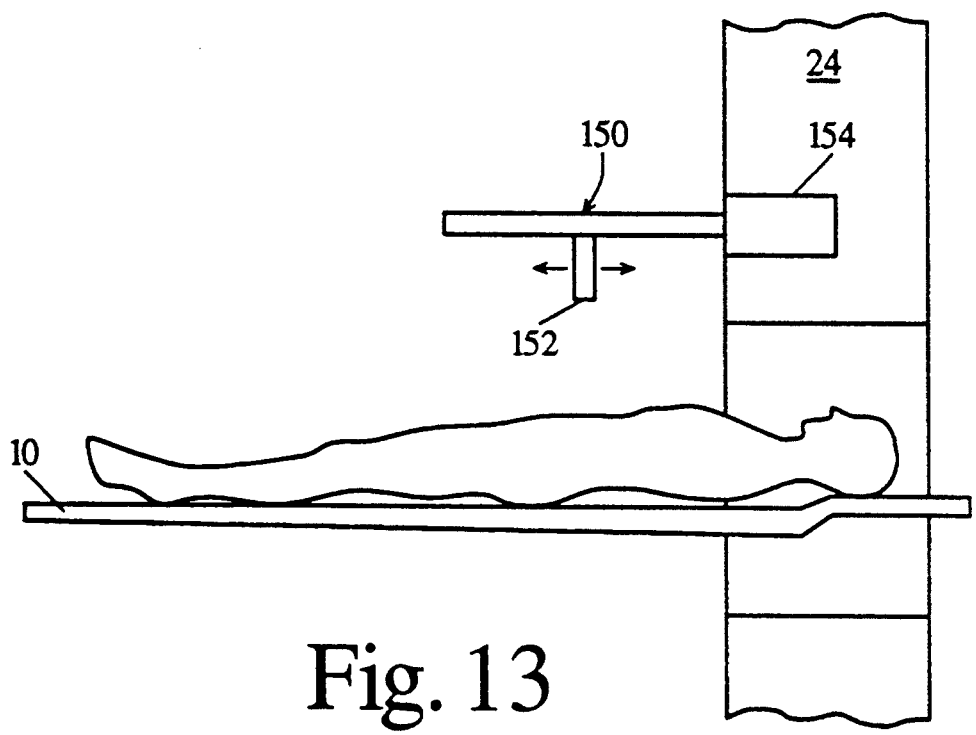
FIG. 13 is a side detailed illustration of the patient periphery measuring means of FIG. 12.
Figure 14:
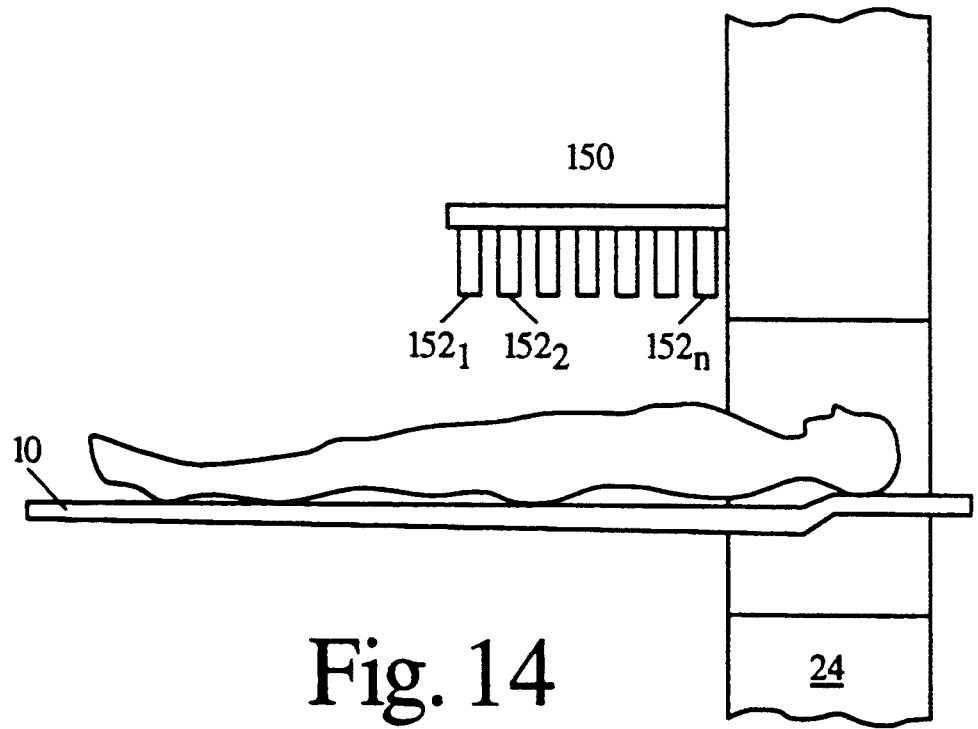
FIG. 14 illustrates an alternate embodiment of the patient periphery measuring system of FIG. 13.

Although the above-described method in conjunction with FIG. 11 produces accurate attenuation corrected emission images, still better images can be obtained if the boundary of the subject being examined is determined precisely rather than determined by reconstruction of the incomplete truncated transmission data 88. With reference to FIGS. 12 and 13, an ultrasonic ranging means 150 is mounted between any two of the detector heads 22a, 22b, 22c. In the preferred embodiment, the ultrasonic ranging means includes a single ultrasonic ranging sensor 152. The ranging sensor 152 rotates with the gantry 24 along a circular path. As the ranging sensor rotates, it measures the distance between the circular path traveled by the ranging sensor and the surface of the examined subject. The difference between the radius of the circular path and the surface contour measured by the ranging sensor is an outline contour and position of the examined subject relative to the center of rotation. In the preferred embodiment, an indexing means 154 increments a single ultrasonic ranging sensor means 152 to determine the periphery of the subject at several points along the axial direction. Optionally, as illustrated in FIG. 14, a plurality of ranging sensors 152, 152a, . . . , 152n may be provided.

With reference again to FIG. 11, an outline determining means 160 determines the outline of the subject relative to the center of rotation, hence, in the coordinate system of the reconstructed transmission data. The iterative transmission data reconstruction means 90'' uses the iterative reconstruction of Equation (5) above, but superimposes the boundary constraints from means 160. For example, the pixel values outside of the boundary of the examined subject are set to zero. A substantial percentage of the truncation artifacts appear as fictitious pixel values outside of the true periphery of the subject, e.g., artifact rings. By setting all pixels outside of the true surface of the examined subject to zero, these artifacts are eliminated. In this manner, yet more accurate attenuation coefficients $\mu_{ij}$ are generated for storage in memory 92''.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A method of determining an emission source distribution within a subject, the method comprising:

transmitting radiation photons through the subject;

from a multiplicity of angular positions around the subject, detecting transmission radiation photons which have passed through a central portion of the subject; at some of the angular positions also detecting transmission radiation photons which have passed through edge portions of the subject; and at least at some of the angular positions around the subject, transmission radiation photons through at least some edge portions are not detected;

determining radiation attenuation coefficients from the detected transmission radiation photons, whereby the radiation attenuation coefficients contain artifacts attributable to detection of transmission radiation photons which have traversed the parts of the subject edge portions at only some angular positions and not at others;

determining weighting factors from the artifact containing attenuation coefficients;

detecting emission radiation photons emitted by emission sources distributed within at least the central portion of the subject;

from the detected emission radiation photons and the weighting factors, reconstructing attenuation corrected representation of the emission source distribution in the subject.

2. The method as set forth in claim 1 wherein the emission radiation reconstructing step further includes reconstructing the emission radiation photons using iterative expectation maximization.

3. The method as set forth in claim 2 wherein the attenuation coefficient determining step includes reconstructing the transmission radiation photons using iterative expectation maximization.

4. The method as set forth in claim 3 wherein the iterative expectation maximization includes calculating the value of each radiation attenuation coefficient $\mu_{ij}$ in accordance with:

$$\mu_{ij}^{n+1} = \frac{\mu_{ij}^n}{\sum_{k',m'} W_{ij}^{k'm'}} \sum_{k,m} \left[ W_{ij}^{km} \frac{P_{km}}{P_{km}^t} \right],$$

where $$P_{km} = \sum_{i,j} W_{ij}^{km} \mu_{ij},$$

$W^{km}{}_{ij}$ is a corresponding weighting factor, n+1 indicates the present iteration, and n indicates a preceding iteration.

5. The method as set forth in claim 1 further including:

measuring an actual periphery of the subject;

using the measured actual periphery of the subject in conjunction with determining the radiation coefficients from the detected transmission photons.

6. The method as set forth in claim 5 wherein the calculating of the weighting factors includes:

calculating an array of attenuation factors from the attenuation coefficients by calculating a line integral of the attenuation along a ray extending through each pixel to a radiation detector;

determining the weighting factors from the attenuation factors.

7. A method of determining an emission source distribution within a subject, the method comprising:

transmitting a beam of radiation through the subject which beam is truncated such that it has at least one dimension smaller than a maximum cross-sectional dimension of the subject;

at a plurality of angular orientations around the subject, detecting transmission radiation which have passed through a central portion of the subject such that due to the beam truncation no transmission radiation passing through edge portions of the subject at some angular orientations are detected;

measuring an actual periphery of the subject;

from the detected transmission radiation and the measured actual periphery, determining radiation attenuation properties of the subject;

detecting emission radiation photons emitted by emission sources distributed within the central and edge portions of the subject;

from the detected emission radiation photons and the determined attenuation properties of the subject, reconstructing pixels of an attenuation corrected representation of the emission source distribution in the subject.

8. The method as set forth in claim 7 wherein the reconstructing step includes determining by an iterative estimation each pixel value of the emission source distribution based on prior estimations and the radiation attenuation properties.

9. The method as set forth in claim 7 wherein the step of determining radiation attenuation properties from the transmission radiation includes iteratively estimating radiation attenuation properties of each pixel.

10. The method as set forth in claim 7 wherein the step of measuring the actual periphery of the subject is performed by ultrasonic ranging.

11. A method of reconstructing emission projection signals from a gamma camera system to produce a pixelized image of a distribution of emission sources in an attenuating medium, the method comprising:

rotating at least one head around the medium;

as the at least one head is rotated, simultaneously (i) transmitting radiation through a central portion of the medium to one of the heads such that the at least one head does not receive radiation that was transmitted through peripheral portions of the medium in at least some angular orientations of the at least one head around the medium and (ii) receiving emission radiation from the emission sources distributed in the medium with the at least one head such that transmission and emission projection data are simultaneously collected;

determining cross-talk corrections from the simultaneously collected transmission and emission projection data to correct for transmission radiation contributions to the emission projection data and emission radiation contributions to the transmission projection data;

correcting the transmission and emission projection data with the cross-talk corrections;

generating attenuation coefficients from the transmission data;

from the emission projection data and the attenuation coefficients, reconstructing an image space representation of the distribution of emission sources in the medium.

12. A gamma camera system comprising:
a plurality of gamma camera heads facing an examination region for receiving emission radiation emitted from a subject in the examination region;
a transmission radiation source disposed across the examination region opposite at least a first of the heads;
a circumferential moving means for moving the heads and the transmission radiation source circumferentially around the examination region;
a collimating means for collimating emission and transmission radiation received by at least the first head such that at some circumferential orientations around the examination region, the first head receives transmission radiation from only a portion of the subject and at other circumferential orientations around the examination region, the first head receives transmission radiation from a larger portion of the subject;
a first reconstruction means for reconstructing received transmission radiation data from at least the first head to generate an indication of radiation attenuation properties of the subject, which radiation attenuation properties tend to include artifacts attributable to the collection of transmission radiation data which has passed through different portions of the subject at different circumferential orientations;
a second reconstruction means for processing emission radiation data from the heads and the artifacted attenuation properties to generate an attenuation corrected image representation of emission radiation distribution in the examination region.

13. The system as set forth in claim 12 further including a means for determining an actual periphery of the subject, the first reconstructing means being operatively connected with the means for determining the actual periphery for using the determined actual periphery to reduce artifacts in the attenuation properties.

14. The system as set forth in claim 13 wherein the actual periphery determining means includes an ultrasonic ranging means.

15. The system as set forth in claim 13 wherein the first reconstructing means uses an iterative estimation process to determine the attenuation properties at each of a multiplicity of pixels in the examination region.

16. The system as set forth in claim 15 wherein the second reconstructing means includes an iterative estimating means for iteratively estimating each pixel value of the emission radiation distribution.

17. The system as set forth in claim 12 wherein the first reconstruction means reconstructs attenuation coefficients and further including:
a means for calculating an array of attenuation factors from the attenuation coefficients by calculating a line integral of the attenuation along rays from an entrance point into each pixel to the head;
a means for determining weighting factors from the attenuation coefficients, the weighting factors being the attenuation properties processed by the second reconstruction means.

18. The gamma camera system as set forth in claim 12 wherein the collimator means is mounted on the radiation receiving face of at least the first gamma camera head, the collimator means mounted to the first gamma camera head being one of:
a fan beam collimator;
a cone beam collimator;
a variable focal length;
an astigmatic collimator; and,
a parallel collimator.

19. The gamma camera system as set forth in claim 18 wherein the transmission radiation source includes one of:
a line source;
a bar source;
a point source;
a flat rectangular-shaped source which is small compared to an entrance surface of the collimator means;
a disk source which is small compared to an entrance surface of the collimator; and,
a flood source.

20. The gamma camera system as set forth in claim 12 further including a source collimator means for restricting radiation from the transmission radiation source to impinge on the first head across the examination region therefrom.

21. The gamma camera system as set forth in claim 12 further including:
a means for moving the radiation source toward and away from the examination region.

22. The gamma camera system as set forth in claim 21 further including:
a radial moving means for moving the gamma camera heads radially toward and away from the examination region; and,
a control means for controlling at least the radiation source moving means and the radial moving means such that the radiation source and the opposite head maintain a fixed spacing relative to each other.

23. A gamma camera system comprising:
a plurality of gamma camera heads facing an examination region for receiving emission radiation emitted from a subject in the examination region;
a transmission radiation source disposed across the examination region opposite at least a first of the heads;
a circumferential moving means for moving the heads and the transmission radiation source circumferentially around the examination region;
a collimating means for collimating emission and transmission radiation received by the gamma camera heads;
a means for determining an actual periphery of the subject;
a first reconstruction means for reconstructing received transmission radiation data from at least the first head and the actual periphery determined by the periphery determining means to generate an indication of radiation attenuation properties of the subject;
a second reconstruction means for processing emission radiation data from the heads and the attenuation properties to generate an attenuation corrected image representation of emission radiation distribution in the examination region.

24. The system as set forth in claim 23 wherein the actual periphery determining means includes an ultrasonic ranging means.

25. In an emission tomographic apparatus which includes a plurality of gamma camera heads, a transmission source opposite at least one of the heads, a means for moving the gamma camera heads and the transmission radiation source around a subject examination region, a collimating means for collimating radiation received by the gamma camera heads, a means for determining an actual periphery of a subject in the examination region, and a reconstruction means for evaluating transmission radiation attenuation properties of transmission radiation received by the at least one gamma camera head and for determining an emission source distribution of radiation emitting sources distributed within the subject, THE IMPROVEMENT COMPRISING:

the reconstruction means using the actual subject periphery determined by the actual periphery determining means and the evaluated transmission radiation attenuation properties for determining the emission source distribution.

* * * * *

UNITED STATES PATENT AND TRADEMARK OFFICE
CERTIFICATE OF CORRECTION

PATENT NO. : 5,338,936
DATED : August 16, 1994
INVENTOR(S) : Gullberg, et al

It is certified that error appears in the above-indentified patent and that said Letters Patent is hereby corrected as shown below:

On Title Page:

[73] Assignee: UNIVERSITY OF UTAH, THE, Salt Lake City, Utah and
PICKER INTERNATIONAL, INC., Highland Heights, Ohio Signed and Sealed this Eighth Day of November, 1994

Attest:

BRUCE LEHMAN

*Attesting Officer*    *Commissioner of Patents and Trademarks*

UNITED STATES PATENT AND TRADEMARK OFFICE
CERTIFICATE OF CORRECTION

PATENT NO.    : 5,338,936
DATED         : August 16, 1994
INVENTOR(S)   : Gullberg et al.

It is certified that error appears in the above-identified patent and that said Letters Patent is hereby corrected as shown below:

Column 1,
Line 3, please insert the paragraph:

-- The U.S. Government has a paid-up license in this invention and the right in limited circumstances to require the patent owner to license others on reasonable terms as provided by the terms of Grant No. R01 HL39792 awarded by the National Institute of Health. --

Signed and Sealed this

Eleventh Day of March, 2003

JAMES E. ROGAN
*Director of the United States Patent and Trademark Office*